US011185215B2

(12) United States Patent
Chu

(10) Patent No.: US 11,185,215 B2
(45) Date of Patent: Nov. 30, 2021

(54) MEDICAL SYSTEMS, DEVICES, AND RELATED METHODS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 462 days.

(21) Appl. No.: 16/054,799

(22) Filed: Aug. 3, 2018

(65) Prior Publication Data

US 2019/0038113 A1 Feb. 7, 2019

Related U.S. Application Data

(60) Provisional application No. 62/542,103, filed on Aug. 7, 2017.

(51) Int. Cl.
| | | |
|---|---|---|
| *A61B 1/00* | (2006.01) | |
| *A61B 1/307* | (2006.01) | |
| *A61B 17/221* | (2006.01) | |
| *G02B 23/24* | (2006.01) | |
| *A61B 1/018* | (2006.01) | |
| *A61B 17/00* | (2006.01) | |

(Continued)

(52) U.S. Cl.
CPC ...... *A61B 1/00121* (2013.01); *A61B 1/00105* (2013.01); *A61B 1/00133* (2013.01); *A61B 1/018* (2013.01); *A61B 1/307* (2013.01); *A61B 17/221* (2013.01); *G02B 23/2476* (2013.01); *A61B 1/00085* (2013.01); *A61B 1/00087* (2013.01); *A61B 1/00135* (2013.01); *A61B 1/2733* (2013.01); *A61B 1/2736* (2013.01); *A61B 5/0084* (2013.01); *A61B 10/06* (2013.01); *A61B 17/3201* (2013.01); *A61B 2017/0034* (2013.01); *A61B 2017/00296* (2013.01); *A61B 2017/00477* (2013.01)

(58) Field of Classification Search
CPC ............ A61B 1/00121; A61B 1/00105; A61B 1/00133; A61B 1/018; A61B 1/307; A61B 1/00112; A61B 1/00128; A61B 1/00131; A61B 1/00135; A61B 2017/00296; A61B 2017/0034
See application file for complete search history.

(56) References Cited

U.S. PATENT DOCUMENTS 6,135,947 A * 10/2000 Watanabe .......... A61B 1/00117
600/160
6,468,285 B1 * 10/2002 Hsu ...................... A61B 17/062
606/158

(Continued)

*Primary Examiner* — Alexandra L Newton
*Assistant Examiner* — Jae Woo
(74) *Attorney, Agent, or Firm* — Bookoff McAndrews, PLLC

(57) ABSTRACT

An adaptor may include a shell and a plunger positioned at a first end of the shell and moveable between an undepressed state and a depressed state. The adaptor may further include a ramp extending from a second end of the shell and a carrier coupled to the ramp. In the undepressed state, the carrier may be located at a first position along the ramp, and wherein, in the depressed state, the carrier may be located at a second position along the ramp, wherein the second position may be closer to the second end of the shell than the first position.

14 Claims, 10 Drawing Sheets

(51) Int. Cl.
  *A61B 17/3201* (2006.01)
  *A61B 5/00* (2006.01)
  *A61B 1/273* (2006.01)
  *A61B 10/06* (2006.01)

(56) References Cited

U.S. PATENT DOCUMENTS

| | | | | |
|---|---|---|---|---|
| 7,553,319 | B2* | 6/2009 | Bagaoisan | A61M 25/10182 |
| | | | | 606/214 |
| 8,021,293 | B2* | 9/2011 | Dejima | A61B 1/0055 |
| | | | | 600/104 |
| 9,289,195 | B2* | 3/2016 | Bagaoisan | A61B 17/0057 |
| 9,339,411 | B2* | 5/2016 | Stout | A61F 6/225 |
| 10,201,265 | B2* | 2/2019 | Dickhans | A61B 1/018 |
| 10,321,923 | B2* | 6/2019 | DeGraaf | A61B 17/221 |
| 10,524,770 | B2* | 1/2020 | Chu | A61B 17/00234 |
| 10,561,463 | B2* | 2/2020 | Dickhans | A61B 1/00133 |
| 10,687,828 | B2* | 6/2020 | Greenhalgh | A61B 17/00234 |
| 2003/0204188 | A1* | 10/2003 | Morrison | A61B 18/148 |
| | | | | 606/45 |
| 2006/0224041 | A1* | 10/2006 | Okada | A61B 10/06 |
| | | | | 600/106 |
| 2006/0247494 | A1* | 11/2006 | Nakagawa | A61B 18/1492 |
| | | | | 600/104 |
| 2006/0247495 | A1* | 11/2006 | Bacher | A61B 18/1445 |
| | | | | 600/106 |
| 2007/0203393 | A1* | 8/2007 | Stefanchik | A61B 1/018 |
| | | | | 600/106 |
| 2007/0225555 | A1* | 9/2007 | Stefanchik | A61J 15/003 |
| | | | | 600/104 |
| 2008/0200756 | A1* | 8/2008 | Okada | A61B 1/018 |
| | | | | 600/106 |
| 2008/0262293 | A1* | 10/2008 | Murakami | G02B 23/2476 |
| | | | | 600/102 |
| 2008/0275483 | A1* | 11/2008 | Makower | A61B 18/12 |
| | | | | 606/192 |
| 2008/0319260 | A1* | 12/2008 | Murakami | A61B 90/98 |
| | | | | 600/106 |
| 2009/0118575 | A1* | 5/2009 | Ichikawa | A61B 1/0051 |
| | | | | 600/103 |
| 2009/0138025 | A1* | 5/2009 | Stabler | A61B 34/30 |
| | | | | 606/130 |
| 2010/0094167 | A1* | 4/2010 | Iinuma | A61B 1/00082 |
| | | | | 600/567 |
| 2010/0228085 | A1* | 9/2010 | Mirza | A61B 1/00087 |
| | | | | 600/106 |
| 2011/0028894 | A1* | 2/2011 | Foley | A61B 34/30 |
| | | | | 604/95.01 |
| 2012/0078080 | A1* | 3/2012 | Foley | A61B 34/30 |
| | | | | 600/411 |
| 2012/0136207 | A1* | 5/2012 | Goldfarb | G02B 6/4292 |
| | | | | 600/106 |
| 2014/0171833 | A1* | 6/2014 | Matsuno | A61B 17/320016 |
| | | | | 600/585 |
| 2014/0257253 | A1* | 9/2014 | Jemison | A61B 17/32056 |
| | | | | 606/1 |
| 2015/0119895 | A1* | 4/2015 | Tah | A61B 17/221 |
| | | | | 606/127 |
| 2015/0164522 | A1* | 6/2015 | Budiman | A61B 17/221 |
| | | | | 606/113 |
| 2016/0089127 | A1* | 3/2016 | Kirkemo | A61B 17/221 |
| | | | | 606/110 |
| 2016/0213387 | A1* | 7/2016 | DeGraaf | A61B 1/018 |
| 2016/0331468 | A1* | 11/2016 | Lee | A61B 34/20 |
| 2017/0188793 | A1* | 7/2017 | Ouyang | A61B 1/00103 |
| 2017/0296271 | A1* | 10/2017 | Chu | A61B 1/00133 |
| 2017/0319221 | A1* | 11/2017 | Chu | A61B 17/221 |
| 2018/0014996 | A1* | 1/2018 | Asbaghi | A61M 5/326 |
| 2018/0043138 | A1* | 2/2018 | Chu | A61M 25/0097 |
| 2018/0125511 | A1* | 5/2018 | Chu | A61B 90/03 |
| 2018/0125516 | A1* | 5/2018 | Chu | A61B 17/221 |
| 2018/0126126 | A1* | 5/2018 | Ornelas Vargas | A61M 39/10 |
| 2018/0168672 | A1* | 6/2018 | Chu | A61B 17/221 |
| 2018/0206863 | A1* | 7/2018 | Chu | A61B 1/0014 |
| 2018/0256180 | A1* | 9/2018 | Tah | A61B 17/221 |
| 2019/0038113 | A1* | 2/2019 | Chu | A61B 1/00133 |
| 2019/0046019 | A1* | 2/2019 | Ito | A61B 1/018 |
| 2019/0274699 | A1* | 9/2019 | Morey | A61B 17/221 |
| 2020/0023163 | A1* | 1/2020 | Chu | A61B 10/06 |
| 2020/0038041 | A1* | 2/2020 | Chu | A61B 17/221 |
| 2020/0197579 | A1* | 6/2020 | Chu | A61M 25/0097 |
| 2020/0359877 | A1* | 11/2020 | Seow | A61B 1/00149 |

\* cited by examiner

MEDICAL SYSTEMS, DEVICES, AND RELATED METHODS

CROSS-REFERENCE TO RELATED APPLICATIONS

This patent application claims the benefit of priority under 35 U.S.C. § 119 to U.S. Provisional Patent Application No. 62/542,103, filed Aug. 7, 2017, which is herein incorporated by reference in its entirety.

TECHNICAL FIELD

Various aspects of the present disclosure relate generally to medical systems, devices, and related methods. More specifically, the present disclosure relates to medical systems and/or devices for treating tissue and/or removing objects within the body of a patient.

BACKGROUND

The field of endoscopy covers systems and methods a user may employ to examine and/or treat a patient with, e.g., the assistance of an endoscope or other suitable introduction sheaths or devices. An endoscope (or other suitable introduction device) may provide for viewing of, for example, the interior of a hollow organ or cavity in the patient's body. Ureteroscopy, for example, may be performed to diagnose and treat urinary tract diseases and ureteral strictures. A ureteroscope may be inserted retrograde through the urinary tract such that diagnosis and treatment of urinary tract abnormalities may be performed. Such procedures, including Flexible Ureterorenoscopy (FURS), often require at least two operators.

For example, a dominant hand of a first medical professional will hold the handle of the ureteroscope while the non-dominant hand holds the distal portion of the ureteroscope as it enters the urinary meatus. If the medical professional determines there is a need to insert a tool or medical device such as a basket, grasper, or forceps through the working channel of the scope, he or she is left to either remove the non-dominant hand from the urinary meatus or instruct an assistant to hold the medical device handle. Removing their hand from the urinary meatus, however, removes the medical professional's ability to control the depth of the scope's insertion into the urinary meatus. On the other hand, if the medical professional opts to instruct an assistant to control the medical device, for example, a basket, communication between the medical professional and assistant must be exact and clear, otherwise, the assistant may be required to perform multiple attempts at grasping a stone or other material before successfully capturing the stone or other material within the basket. Multiple attempts frequently result in damaged baskets, increased risk of damage to the patient's surrounding tissue, and increased time of procedure, among others.

The systems, devices, and methods of the current disclosure may rectify some of the deficiencies described above or address other aspects of the prior art.

SUMMARY

Examples of the present disclosure relate to, among other things, medical devices. Each of the examples disclosed herein may include one or more of the features described in connection with any of the other disclosed examples.

In one example, an adaptor may include a shell and a plunger positioned at a first end of the shell and moveable between an undepressed state and a depressed state. The adaptor may further include a ramp extending from a second end of the shell and a carrier coupled to the ramp. In the undepressed state, the carrier may be located at a first position along the ramp, and wherein, in the depressed state, the carrier may be located at a second position along the ramp, wherein the second position may be closer to the second end of the shell than the first position.

Examples of the adaptor may include one or more of the following features. A cable may be coupled to the carrier and a sleeve coupled to the ramp. In the depressed state, more of the cable may extend exterior of the sleeve than in the undepressed state. The ramp may include a slit fixedly coupled to the sleeve. The plunger may be snap-fit or friction-fit within a channel of the adaptor. The ramp may include at least one rail received within a channel of the carrier. The ramp may include a curved support guide. The adaptor may further include a medical device handle coupled thereto. The medical device handle may include a sheath moveable with respect to a shaft between a collapsed configuration and an expanded configuration. The sheath of the medical device handle may be removably coupled to the carrier. The medical device may include a stationary plunger and a body movable with respect to the stationary plunger. The adaptor may further include a track. The track may include a portion extending from the plunger toward the ramp and a portion extending from the first portion and along the ramp. A cable may extend from the plunger, through the track, and may be coupled to the carrier. The shell may be snap-fit on an insertion device.

In a further aspect, a method may include positioning an end of a shaft of a medical device at a location relative to an end of a shaft of an insertion device. Additionally, the method may include coupling a handle of the medical device to a handle of the insertion device via an adaptor. Further, the method may include depressing a plunger of the adaptor so as to adjust the location and actuating the medical device handle to deploy an end-effector distally of the shaft of the medical device.

Examples of the method may include one or more of the following features. Coupling the handle of the medical device to the handle of the insertion device may include compressing the adaptor towards the handle of the insertion device. The method may further include coupling the shaft of the medical device with a carrier of the adaptor. Depressing the plunger may move the carrier relative to a ramp of the adaptor.

In a further example, an adaptor may include a shell extending between a first end and a second end and a plunger positioned at the first end of the shell and moveably received within a channel of the shell. The adaptor may further include a ramp extending from the second end of the shell and a carrier movably coupled to the ramp. Additionally, the adaptor may include a cable extending from an end of the channel, through the plunger, and coupled to the carrier.

Examples of the adaptor may include one or more of the following features. The plunger may be moveable relative to the cable. The ramp may include a curved support guide. The adaptor may have a sleeve and a first end of the sleeve may be coupled to the plunger and the second end of the sleeve may be coupled to the ramp. The plunger may be snap-fit or friction-fit within the channel.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical systems and devices for diagnosing and/or treating internal areas of a patient's body. The medical system may include an insertion device and one or more medical devices operably coupled thereto for introduction of an end-effector or other object through the insertion device.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to a medical professional using the medical device or insertion device. In contrast, "distal" refers to a position relatively further away from the medical professional using the medical device or insertion device, or closer to the interior of the body.

Figure 1A:
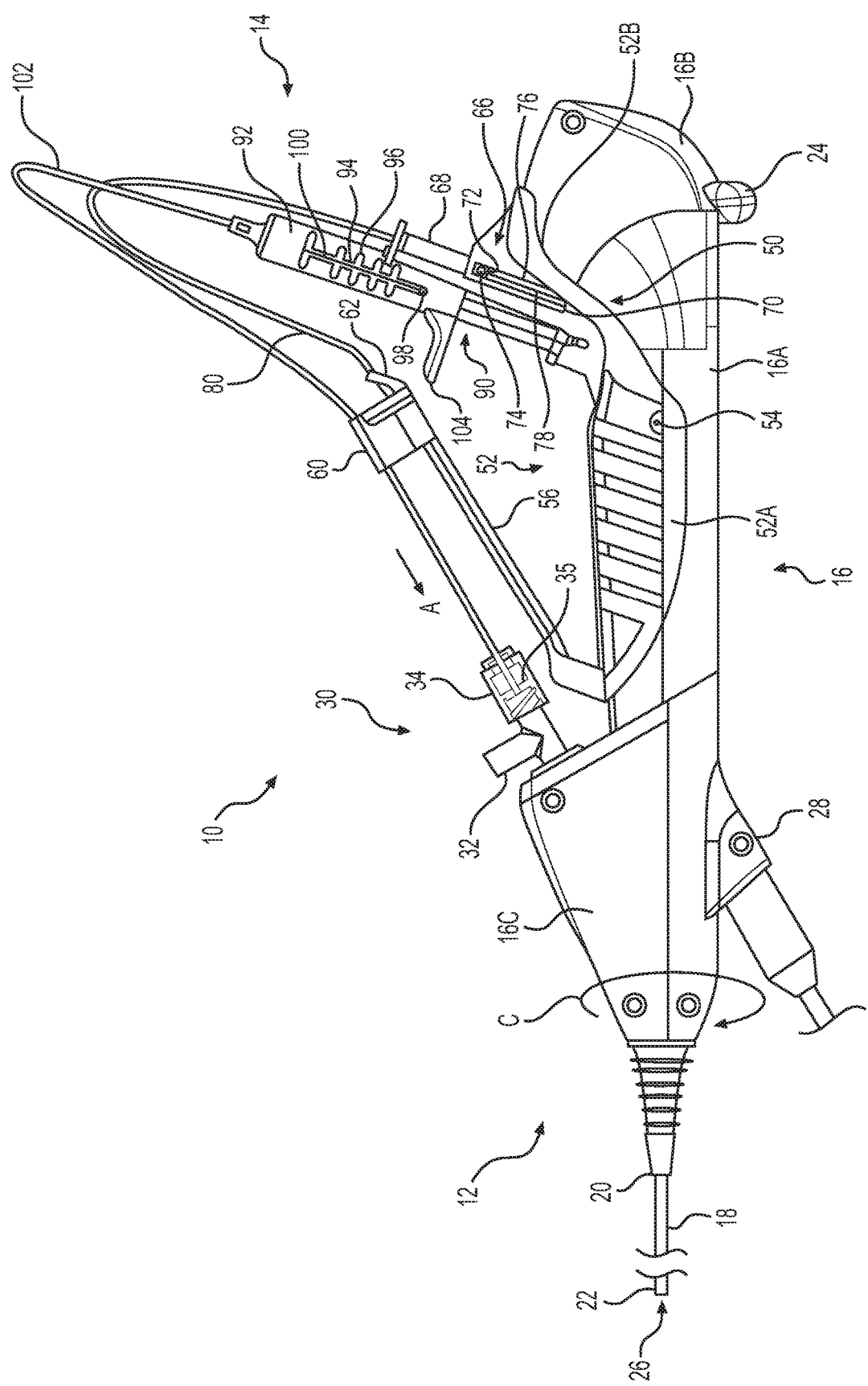
FIG. 1A illustrates an exemplary system including a medical device in a retracted configuration and coupled to an insertion device via an adaptor.
Figure 1B:
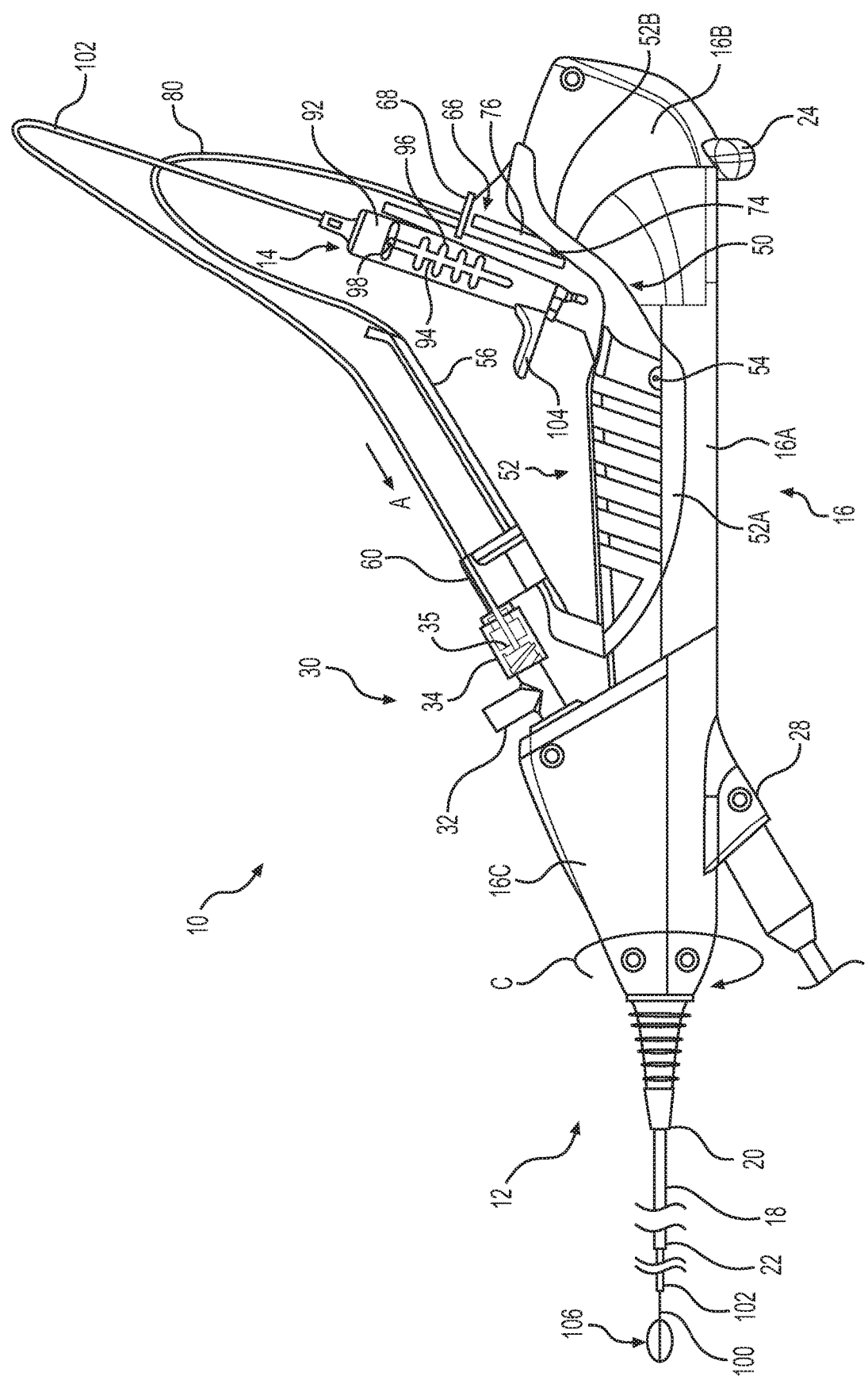
FIG. 1B illustrates the system of FIG. 1A with the medical device in an extended configuration.

FIGS. 1A and 1B illustrate an exemplary system 10 including an insertion device 12 and a medical device 14. Insertion device 12 may include any device configured to allow an operator to perform medical diagnoses and/or treatments on a subject. For example, insertion device 12 may include any device configured to allow a user to access and view internal areas of a subject's body. Additionally or alternatively, insertion device 12 may itself be a medical device and/or include any device configured to deliver one or more medical devices 14, such as, for example, biopsy forceps, graspers, baskets, snares, probes, scissors, retrieval devices, lasers, and/or other tools, into a subject's body. Insertion device 12 may be inserted into one of a variety of body openings, lumens, and/or cavities. For example, insertion device 12 may be inserted into any portion of a urinary tract, such as a ureter, a gastrointestinal lumen, such as an esophagus, a vascular lumen, and/or an airway.

According to aspects of the present disclosure, insertion device 12 may be a ureteroscope. In some contemplated examples, insertion device 12 may be a sterile, single-use, and disposable ureteroscope or a multiple-use, non-disposable ureteroscope. Other types of devices, however, may be substituted for the ureteroscope, including, as examples, a hysteroscope, a uteroscope, a bronchoscope, a cystoscope, and similar devices. Such devices may be single-use and disposable, or multiple-use and non-disposable.

A handle 16 of insertion device 12 may have any shape suitable for gripping and controlling insertion device 12. For example, handle 16 may have an ergonomic shape including a grip portion 16A designed to be held comfortably in the hand, e.g., the palm of the hand. Handle 16 may further include an actuator portion 16B extending from a first end of grip portion 16A, and a port coupling portion 16C extending from an opposite end of grip portion 16A. Shaft 18 may extend from a proximal end 20 to a distal end 22, such that proximal end 20 of shaft 18 may be coupled to (e.g., detachably or permanently connected to) a distal end of handle 16. Insertion device 12 may include a steering mechanism for deflecting shaft 18 along one or more planes. For example, handle 16 may include an actuator 24 coupled to one or more portions of shaft 18 at or near distal end 22 via one or more control members, such as steering wires (not shown). Any suitable steering mechanism and/or actuators may be used.

Shaft 18 may include at least one working channel 26 extending between proximal end 20 and distal end 22 of shaft 18. While only a single working channel 26 is described, working channel 26 may be a primary working channel for delivery of one or more medical devices 14 while additional channels (not shown) also may extend between proximal end 20 and distal end 22 of shaft 18. Such additional channels may have different shapes and/or sizes. In some examples, shaft 18 may include one or more electronic components, such as a camera or other imaging device, a light source, and/or other sensor (not shown). Additionally or alternatively, one of the additional channels may provide a lumen for light delivery and/or steering control members (not shown) associated with actuator 24 for steering shaft 18.

Handle 12 may include an umbilicus hub or connector 28 for facilitating electrical connections and functions, such as transferring data and/or powering a light source. In addition, handle 12 may include at least one port coupling 30 (e.g., a T-shaped or Y-shaped female luer port connection). Port coupling 30 may include a first branch 32 which may be fluidly coupled to one or more sources of irrigation and/or suction fluid. Accordingly, irrigation fluid (not shown) may be delivered (e.g., pumped) through working channel 26, via first branch 32 to provide lubrication and/or aid in visualization. Port coupling 30 may also include a second branch 34 in communication with working channel 26, e.g., to allow for the insertion of one or more medical device(s) 14 through working channel 26 toward distal end 22 of shaft 18. As shown, second branch 34 may include a wiper seal and/or valve 35 comprised of silicone or low durometer rubber material to prevent backflow of fluid from the subject's body. Valve 35 may include a small opening through which an end-effector 106, shaft 100, and sheath 102 of medical device 14 may be inserted in any appropriate manner.

Figure 2:
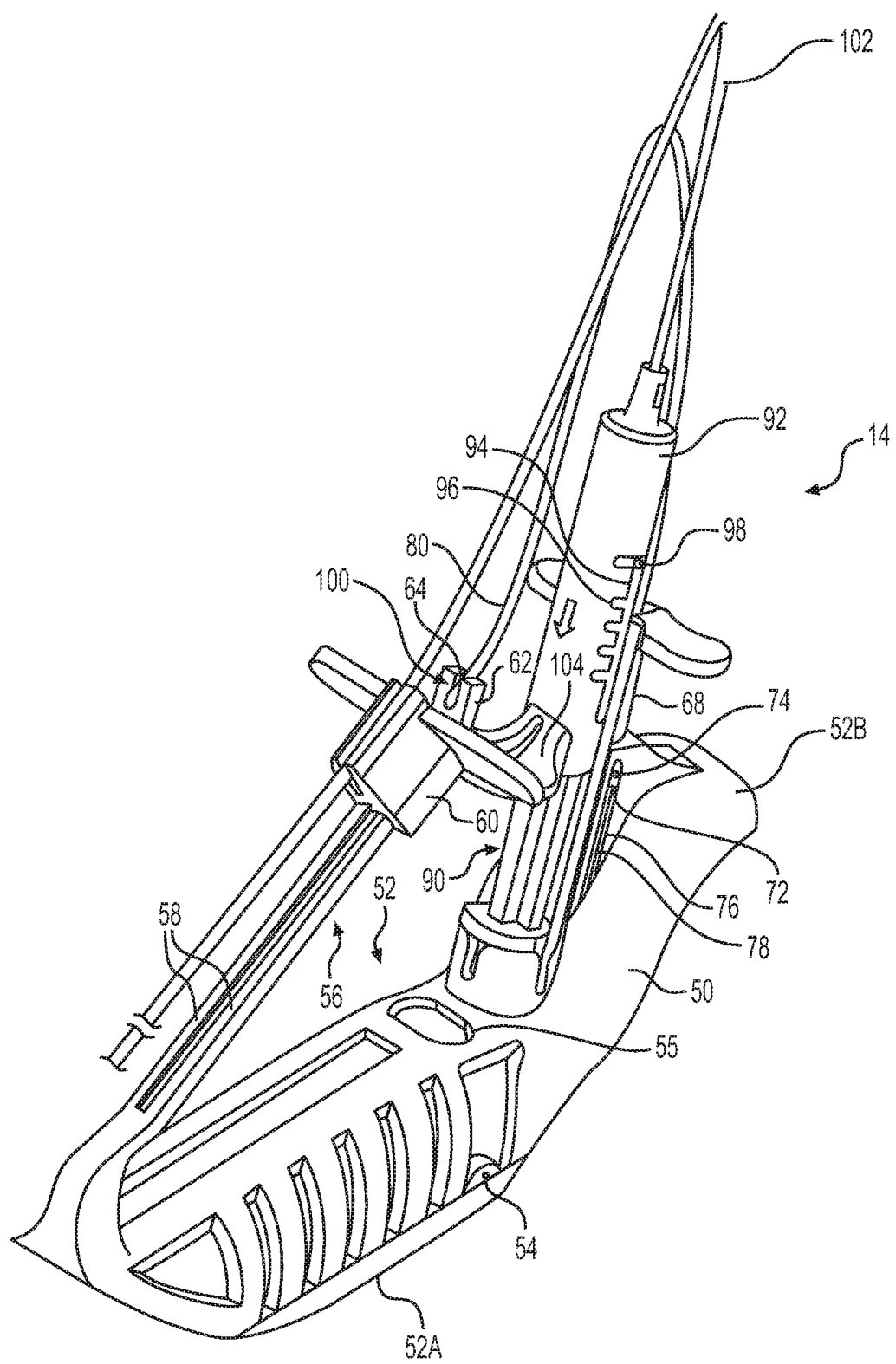
FIG. 2 illustrates the adaptor of FIGS. 1A and 1B uncoupled from the insertion device.

As shown in FIGS. 1A and 1B, an adaptor 50 may be selectively coupled to handle 16 of insertion device 12. FIG. 2 shows adaptor 50 separated from handle 16. Adaptor 50 includes a flexible shell 52. Shell 52 may be contoured to correspond to the shape of handle 16. For example, shell 52 may include a main portion 52A corresponding in shape/arrangement to grip portion 16A and an actuator portion 52B corresponding in shape/arrangement to actuator portion 16B. Shell 52 may be snap-fit or otherwise coupled to handle 16. For example, shell 52 may flex outwardly to receive handle 16 therein, as will be described in further detail below. Additionally, shell 52 may include a protrusion, extension, and/or pin 54 extending radially inwardly toward a longitudinal axis of shell 52. While only one pin 54 is illustrated, it is understood that additional pins 54 may be used. For example, two diametrically opposed pins 54 may be arranged on opposite sides of adaptor 50. Upon coupling adaptor 50 to handle 16, pin 54 may be received within an opening, passage, recess, or hole (not shown) of handle 16 aligned with pin 54. In such a manner, pin 54 may comprise an alignment mechanism facilitating accurate and consistent coupling of adaptor 50 to handle 16. Alternatively, as shown in FIG. 2, adaptor 50 may remain uncoupled from handle 16. In such an arrangement, medical device 14 may be operated via another medical professional and/or an additional hand of the medical professional operating insertion device 12, as will be described in further detail below. Further, as shown in the orientation of FIG. 2, adaptor 50 may include one or more openings 55, through which one or more buttons/actuators may extend. The arrangement, size, and/or shape of openings 55 may be selected based on the arrangement, size, and/or shape of any such buttons/actuators (not shown) of insertion device 12.

A distal end of adaptor 50, opposite actuator portion 52A, is coupled to or monolithically formed with, a ramp 56. Ramp 56 extends at an angle generally parallel with an angle of second branch 34 and includes a pair of rails 58 (FIG. 2) upon which a carrier 60 may be slidingly received, as will be described in further detail below. A free end 62 (e.g., an end of ramp 56 uncoupled to a remainder of adaptor 50) may extend at an angle to a remainder of ramp 56. That is, free end 62 may include a bent flange or tab which may be coupled to a sleeve 80 via a slot 64 (FIG. 2), as will be described in further detail below.

Actuator portion 52B of adaptor 50 further includes a channel 66. A plunger 68 of adaptor 50 may be movably received within channel 66. For example, plunger 68 may be moveable between an extended state, as shown in FIG. 1A, and a depressed state, as shown in FIG. 1B. In some arrangements, a spring or other such biasing member (not shown) may be received within channel 66 between an end 70 of channel 66 and an end 72 of plunger 68 so as to bias plunger 68 toward the extended state. In other arrangements, such a biasing member may be omitted. A pair of pins or other such protrusions 74 of plunger 68 may be received within a slot 76 of adaptor 50 so as to maintain rotational alignment of plunger 68 relative to channel 66, as will be described in further detail below.

An operating member, lead, cable, and/or wire 78 (e.g., a flexible, super elastic Nitinol wire) includes a length extending from a first end mounted or coupled to end 70 of channel 66 in any appropriate manner (e.g., solder, tying, heat-staking, adhesives, or the like), through plunger 68 (e.g., through an opening 82 (FIG. 3) of plunger 68), and to a second end mounted or coupled to carrier 60 in any appropriate manner (e.g., solder, tying, heat-staking, adhesives, or the like). Wire 78 is curved or in an arc configuration as shown in FIGS. 1A and 1B and is longer than necessary to extend between end 70 and carrier 60. At least a portion of wire 78 is moveably received within sleeve 80. Sleeve 80 may be, for example, a flexible sleeve comprised of any appropriate material (e.g., polymer), and may be shaped in a manner similar to wire 78. That is, sleeve 80 may follow the same curved or arc-shaped path as wire 78. For example, as noted above, sleeve 80 may have a sleeve length extending from a first end of sleeve 80 coupled to free end 62 via slot 64 and to an opposite end of sleeve 80 coupled to plunger 68 via a slit 84 (FIG. 3) and/or via any other appropriate manner (e.g., adhesive). As wire 78 extends through an assembly (including sleeve 80, plunger 68, and slot 76), wire 78 is longer than sleeve 80 alone. As such, when plunger 68 is extended (e.g., not depressed as shown in FIG. 1A), the arc of sleeve 80 and wire 78 is used to provide "slack" so as to allow movement of plunger 68. Depression of plunger 68, having sleeve 80 coupled thereto, results in the shortening of the assembly relative to wire 78 by a length equal to the depressed distance/length of the plunger 68, thereby creating an offset length between the wire 78 and sleeve 80. The positive offset length of wire 78 will extend from the end of sleeve 80 coupled to free end 62. The offset extension of wire 78 relative to sleeve 80, which is coupled to free end 62, will cause displacement movement of carrier 60 relative to ramp 56 in direction A, as shown in FIG. 1B. Extension of plunger 68 from the depressed state (FIG. 1B) towards the extended state (FIG. 1A) will cause movement of carrier 60 relative to ramp 56 in a direction opposite of direction A.

As shown in FIG. 1A, adaptor 50 further includes medical device 14. As shown, medical device 14 includes a plunger 90 and a slot body 92 moveable with respect thereto. Slot body 92 includes a track 94 extending along a longitudinal axis, and a plurality of slots 96 extending at an angle relative to track 94. For example, slots 96 may extend at an angle generally perpendicular to the longitudinal axis of track 94. Plunger 90 further includes a protrusion or pin 98 located within track 94 or one of the plurality of slots 96. A distal end of plunger 90 may be coupled with a cable, wire, or shaft 100 of medical device 14 while a distal end of slot body 92 may be coupled with a sleeve, tube, or sheath 102 of medical device 14. A proximal end of slot body 92 may include a trigger or tab 104 to facilitate moving slot body 92 relative to plunger 90. A distal end of shaft 100 terminates in an end-effector 106. For example, end-effector 106 may include a basket (FIG. 1B), snare, forceps, and/or grasper. Slot body 92 (coupled to sheath 102) is moveable relative to plunger 90 (coupled to shaft 100) so as to extend and retract end-effector 106 relative to sheath 102, thereby permitting end-effector 106 to move between a collapsed arrangement within sheath 102 (FIG. 1A) and an expanded arrangement extending distally of sheath 102 (FIG. 1B). Interaction between pin 98 and track 94 and/or slots 96 may guide movement of slot body 92 and sheath 102 relative to plunger 90 and shaft 100. Detailed explanation of the features and manner of operation of medical device 14, including slot body 92 and plunger 90, are detailed in U.S. Provisional Application Nos. 62/347,697; 62/435,101; 62/449,150; and 62/455,355, the contents of all of which are incorporated herein by reference.

Figure 3:
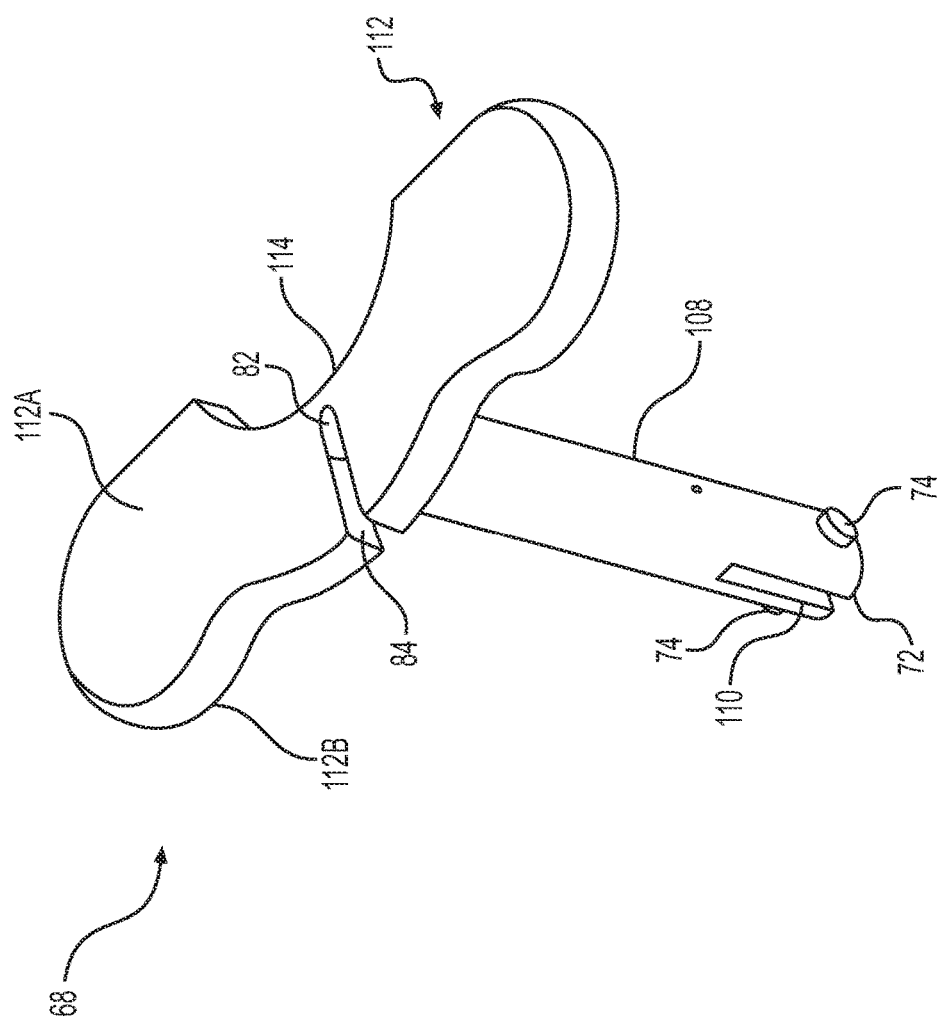
FIG. 3 illustrates an isometric view of a plunger of the adaptor of FIGS. 1A, 1B, and 2.

As shown in FIG. 3, plunger 68 includes an elongate stem 108. A first end of stem 108 includes a slit 110. Each of the pair of protrusions 74 of plunger 68 may be arranged at diametrically opposed locations on stem 108. For example, a first protrusion 74 is located on a first side of slit 110 while a second protrusion 94 is located on a second side of slit 110. Stem 108 of plunger 96 may be snap-fit within channel 66. For example, insertion of stem 108 within channel 66 may compress stem 108 along slit 110 such that stem 108 may be advanced into channel 66. Upon alignment of protrusions 74 with slot 76, stem 108 may return to an uncompressed arrangement, thereby securing plunger 68 to adaptor 50.

Additionally, plunger 68 includes a head 112 extending generally perpendicular to stem 108. Head 112 includes a push surface 112A and a lift surface 112b on opposite sides thereof. Additionally, head 112 includes a contour 114. Upon coupling plunger 68 to adaptor 50, slot body 92 may be received within contour 114. In use, a medical professional may push or depress push surface 112A so as to depress plunger 68, thereby urging carrier 60 in the direction A, as discussed above. In order to withdraw carrier 60, the user may apply an oppositely directed force (e.g., a lifting or upward force) on lift surface 112B so as to move carrier 60 in a direction opposite that of direction A.

Figure 4:
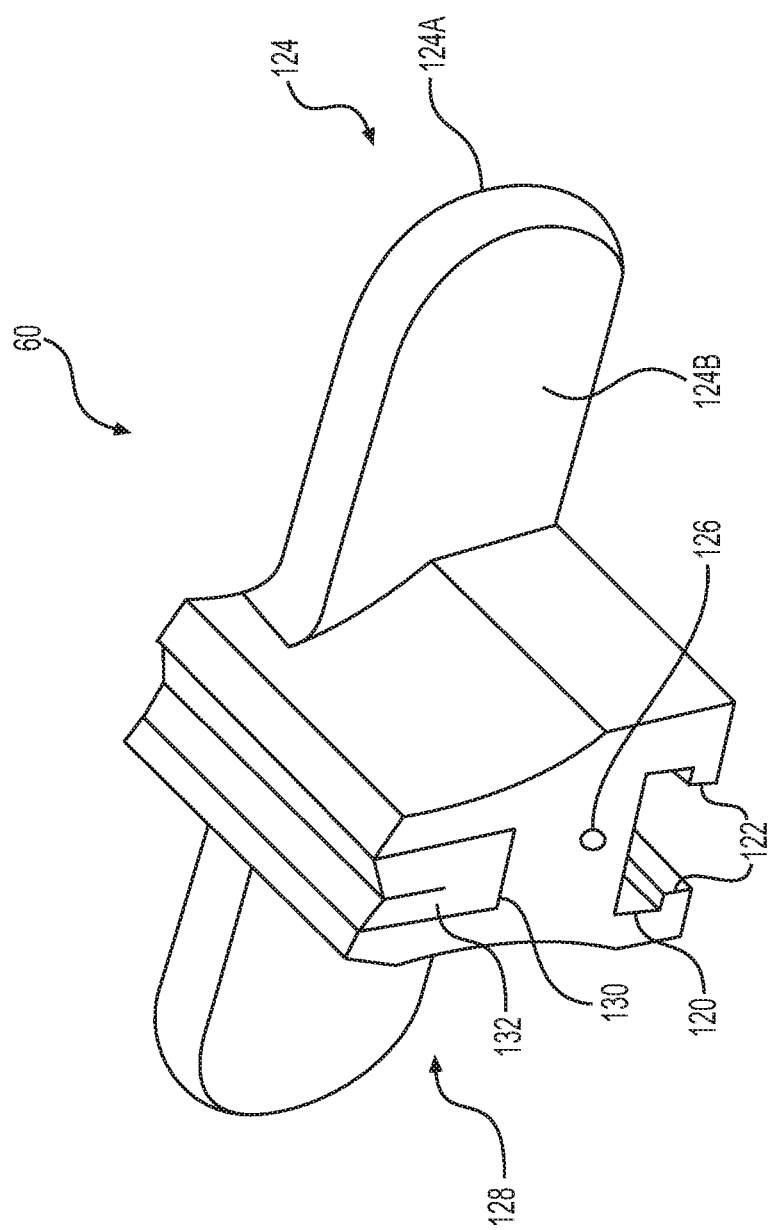
FIG. 4 illustrates an isometric view of a carrier of the adaptor of FIGS. 1A, 1B, and 2.

As shown in FIG. 4, carrier 60, includes a channel 120. Rails 58 of ramp 56 are received within channel 120. For example, channel 120 may wrap around rails 58 while flanges 122 prevent inadvertent separation of carrier 60 from ramp 56. That is, flanges 122 may narrow or constrict a dimension of channel 120 such that upon receipt of rails 58 within channel 120, carrier 60 remains coupled to ramp 56. Similar to plunger 96, carrier 60 includes a head 124 having a push surface 124A and a lift surface 124B on opposite sides thereof. While manipulation of plunger 68 advances or retracts carrier 60, as discussed above, carrier 60 can also be advanced or retracted via application of an appropriate force on head 124 (e.g., as described in connection with FIG. 7). For example, a medical professional may push or depress push surface 124A so as to urge carrier 60 in the direction A. In order to withdraw carrier 60, the user may apply an oppositely directed force (e.g., a lifting or upward force) on lift surface 124B, so as to move carrier 60 in a direction opposite that of direction A. As noted above, carrier 60 is coupled to wire 78. To that end, carrier 60 includes an opening or through hole 126 within which wire 78 may be received. Wire 78 may be secured to carrier 60 within hole 126 via any appropriate manner (e.g., adhesives).

Further, carrier 60 includes a coupler 128. Coupler 128 includes a channel 130 lined with silicone or other such material 132. In use, sheath 102 of medical device 14 may be selectively received within a slit formed by silicone 132. For example, following alignment of a distal end of sheath 102 relative to shaft 18, as will be described in further detail below, sheath 102 may be inserted within channel 130 such that the silicone 132 therein grips and or secures sheath 102 to carrier 60. It is understood that in some arrangements, channel 130 and silicone 132 may be replaced with any appropriate coupling mechanism such that sheath 102 may be selectively coupled and uncoupled with carrier 60. For example, carrier 60 may include a clamp, strap, dumbbell coupler (e.g., FIG. 19) or other such arrangement.

In use, a medical professional may insert insertion device 12 into the body of a patient. For example, shaft 18 of insertion device 12 may be inserted through the urinary meatus of the ureter. Once inserted, the medical professional may optionally deflect distal end 22 of shaft 18 as necessary to direct distal end 22 towards an area or object of interest within the body of the patient via actuator 24 and/or via rotation of handle 16 of insertion device 12.

Next, the medical professional may couple adaptor 50 (if not already done) to handle 16 of insertion device 12. To do so, the medical professional, may retain a grip on gripping grip portion 16A of insertion device 12 with the palm of their hand, while the fingers of the medical professional's hand are opened to grip adaptor 50. The medical professional may the close their hand in the manner of making a fist so as to draw adaptor 50 onto handle 16. That is, adaptor 50 is squeezed onto handle 16. An audible click or snapping sound due to the interaction of pin(s) 54 within correspondingly arranged openings (not shown) on handle 16 may act as an audible or tactile confirmation of the securing of adaptor 50 to handle 16. During the coupling of adaptor 50 to insertion device 12, shell 52 may flex radially outwardly from a longitudinal axis of adaptor 50 and then, when completely coupled, may return to its unflexed arrangement as shown in FIGS. 1A and 1B. That is, a width of an opening of shell 52 may be smaller than a width of handle 16 so that shell 52 is forced to radially expand or open to receive handle 16 therein. In further arrangements, handle 16 can be rotated (e.g., in the direction of arrow C) relative to adaptor 50 so as to selectively couple and uncouple adaptor 50 handle 16. Indicia (FIG. 9) may printed, molded, or the like on adaptor 50 may be used to indicate a direction of arrow C. Alternatively, adaptor 50 may remain uncoupled from handle 16 as shown in FIG. 2. In such an arrangement, adaptor 50, including medical device 14, may be operated by an additional hand of the medical professional or by a secondary medical professional (e.g., an assisting medical professional).

Next, if the medical professional determines there is a need or desire for the insertion of medical device 14, he or she may insert sheath 102 (e.g., manually) through second branch 34 of port coupling 30 and distally through working channel 26 of shaft 18. With the aid of any appropriate visualization technique (e.g., X-ray, magnetic resonance imaging (MRI), ultrasound, a camera of insertion device 12, thermography, etc.), sheath 102 is continuously advanced until at least a distal portion of sheath 102 extends distally and exterior of distal end 22 of shaft 18. Next, sheath 102 may be retracted proximally such that a distal end face of sheath 102 is aligned or approximates the location of distal end 22 of shaft 18. Once sheath 102 and shaft 18 are aligned as desired, sheath 102 may be coupled to carrier 60. For example, sheath 102 may be positioned into channel 130 such that silicone 132 (or other such material) grips sheath 102, thereby retaining a location of sheath 102 relative to shaft 18.

Alternatively, sheath 102 may be secured to carrier 60 at a location indicative of a maximum extent of sheath 102. To do so, carrier 60 may be pushed (e.g., manually advanced via application of force on push surface 124A in the direction A to the farthest extent along ramp 56 (FIG. 1B). Next, the medical professional may extend sheath 102 to the farthest or maximum extent desired distally of (or aligned with) distal end 22 of shaft 18. Once so aligned, sheath 102 may be coupled to carrier 60 via channel 130 and silicone 132 (or via any other such coupling arrangement).

In use, system 10, including adaptor 50 coupled to insertion device 12, may be held similarly to a pistol with the medical professional's pinky, ring, and middle fingers being wrapped about grip portion 16A of handle 16. When the medical professional determines a need or desire to use medical device 14 to treat tissue and/or remove material, the medical professional may depress plunger 68 via his or her index finger. That is, the medical professional may push or apply a force on push surface 112A in a direction toward adaptor 50 so as to shorten the assembly relative to shaft 100. Upon shortening the assembly, wire 78 urges carrier 60 in the direction A along ramp 56 so as to extend sheath 102, coupled to carrier 60, to a desired extent. To retract carrier 60 in a direction opposite that of direction A, the medical professional may use the tops of their fingers or their nail of the index finger to apply an oppositely directed force on lift surfaces 112B. When sheath 102 is appropriately extended or positioned relative to shaft 18, the medical professional may move his or her index finger onto tab 104 to actuate medical device 14. For example, the medical professional may depress tab 104 of slot body 92 so as to expand end-effector 106 of medical device distally of sheath 102. In such a position, end-effector 106 is free to assume an expanded or open configuration, as shown in FIG. 1B. As such, the medical professional may treat the patient with medical device 14 by, for example, capturing a stone or other material within the end-effector 106. The captured stone or material can be released and/or repositioned to another location for further treatment, if necessary. Once a desired treatment is completed, the medical professional may withdraw or remove medical device 14 and/or insertion device 12 from the body of the patient.

Figure 5:
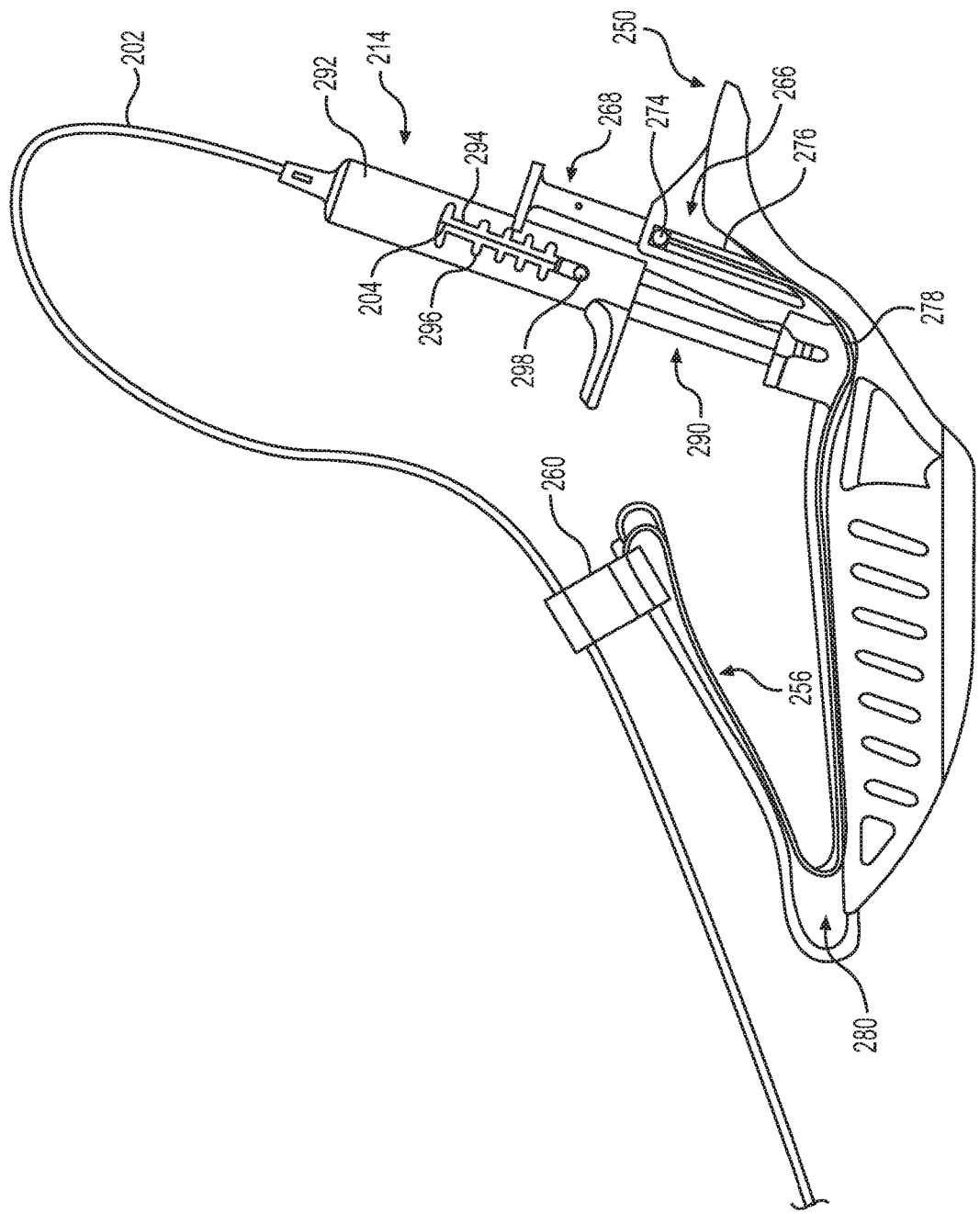
FIG. 5 illustrates an exemplary adaptor according to a further exemplary aspect of the present disclosure.

FIG. 5 illustrates an adaptor 250, according to a further aspect of the disclosure. Adaptor 250, may be selectively coupled and uncoupled from handle 16 of insertion device 12, as described in connection with FIGS. 1A and 1B. Similar to adaptor 50, adaptor 250 includes a medical device 214 including a plunger 290 and a slot body 292 moveable with respect thereto. Slot body 292 includes a track 294 extending along a longitudinal axis, and a plurality of slots 296 extending at an angle relative to track 294, while plunger 290 includes a protrusion or pin 298 located within track 294 or one of the plurality of slots 296. Moreover, similar to medical device 14, medical device 214 includes a sheath 202 coupled to an end of slot body 292 while a shaft 204 is coupled to plunger 290. Slot body 292 (coupled to sheath 202) is moveable relative to plunger 290 (coupled to shaft 204) so as to extend and retract an end-effector (not shown in FIG. 5) relative to sheath 202, thereby permitting the end-effector to move between a collapsed arrangement within sheath 202 (FIG. 5) and an expanded arrangement extending distally of sheath 202.

Additionally, adaptor 250 includes a plunger 268 movably received within a channel 266 with one or more protrusions 274 being located within slot 276 so as to maintain rotational alignment of plunger 268 relative to channel 266. As opposed to medical device 50, however, medical device 214 is coupled to a cable or wire 278 which extends from an end of plunger 268 through channel 266, and through a track 280 extending along adaptor 250. For example, as shown in FIG. 5, wire 278 extends to an end of channel 266 opposite that of plunger 268, and makes a first bend so as to extend distally along main portion 252A of adaptor 250 within track 280. Next, wire 278 makes a second bend and continues to extend within track 280 along ramp 256. Finally, an end of wire 278, opposite the end coupled to plunger 268, is coupled to carrier 260, and carrier 260 may be coupled to ramp 256 in a manner similar to that of carrier 60 and ramp 56 of FIGS. 1A, 1B, and 2. Sheath 202 may also be coupled to carrier 260 in a manner similar to that of sheath 102 and carrier 60, described above. Track 280 may be molded or otherwise formed along adaptor 250 in any appropriate manner. Depression of plunger 268 may urge wire 278 along track 280, and consequently, advance carrier 260 in direction A. Additionally, upon lifting or otherwise retracting plunger 268, wire 278 may be retracted along track 280 so as to retract or withdraw carrier 260 in a direction opposite that of direction A.

Figure 6:
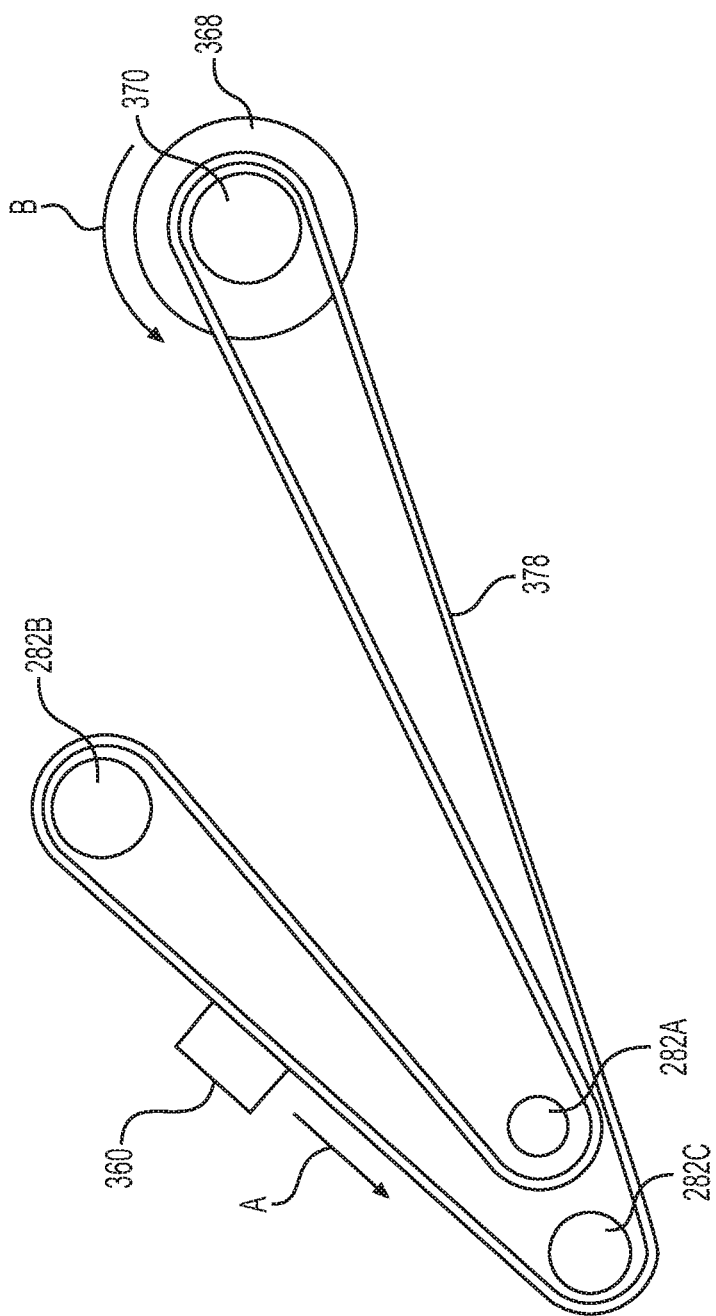
FIG. 6 illustrates an actuation mechanism of an adaptor according to another exemplary aspect of the present disclosure.

FIG. 6 schematically illustrates an alternative actuation mechanism of an adaptor. For example, rather than the use of plunger 68 or 268, a wheel or knob 368 may be used to advance a carrier 360 in direction A. That is, knob 368 may include a post 370 about which cable 378 may be wrapped. Additionally, rather than track 280, a plurality of rotatable members 282A-282C may assist in guiding cable 378. For example, cable 378 may extend from post 370 along a main portion of an adaptor and around member 282A, along a track of an adaptor and around member 282B, then downward along the track of the adaptor and around member 282C, and back toward post 370. In such a manner, rotation of knob 368 in the direction B, will result in advancement of cable 378 about members 282A-282C so as to advance carrier 360 in direction A. Additionally, rotation of knob 368 in a direction opposite that of direction B will result in retraction of cable 378 about members 282A-282C and withdrawal of carrier 360 in a direction opposite that of direction A.

Figure 7:
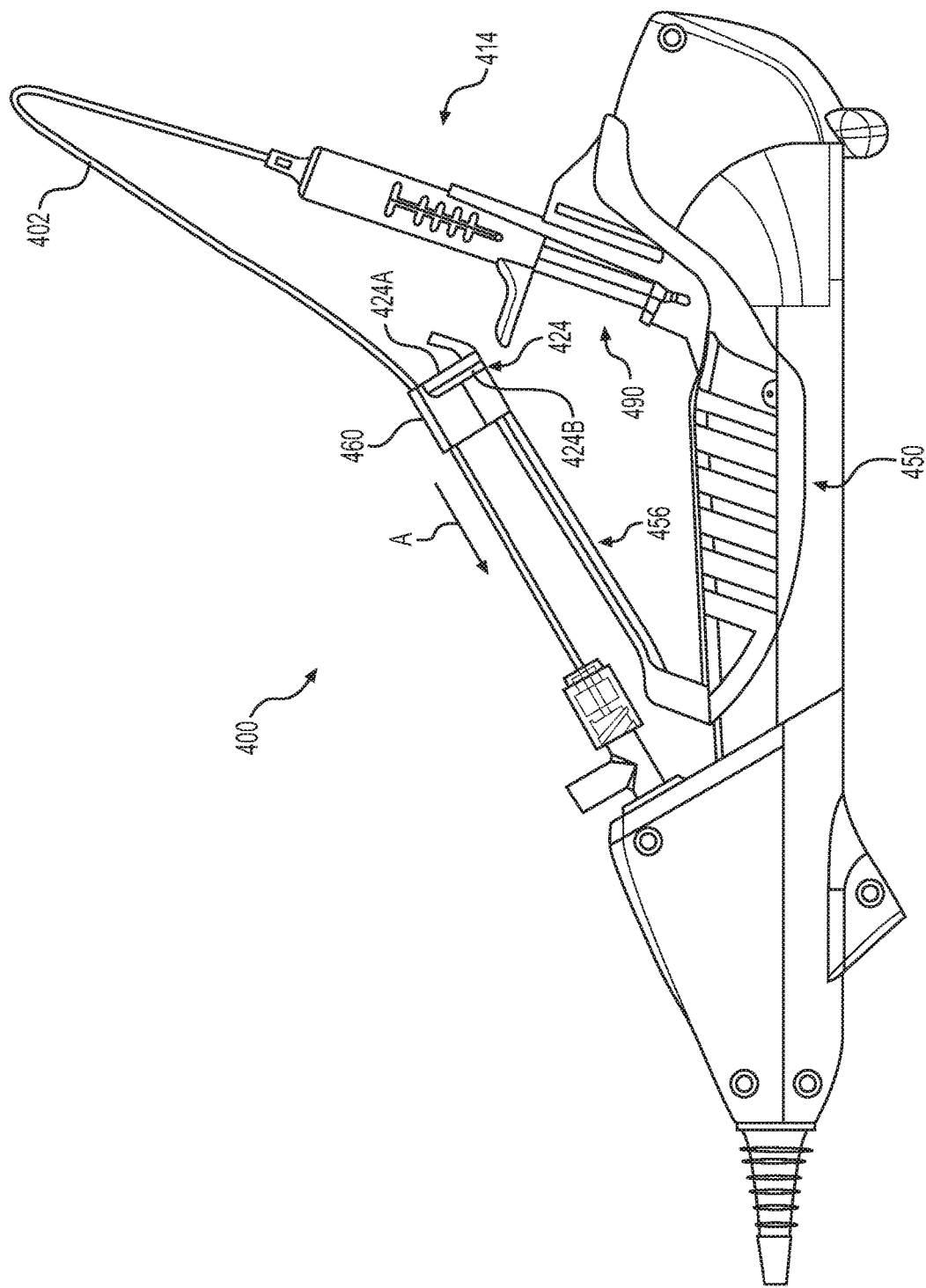
FIG. 7 illustrates an exemplary system according to a further aspect of the present disclosure.

FIG. 7 illustrates a system 400 including a further arrangement of an adaptor 450 including a medical device 414 coupled thereto. Adaptor 450 is similar to adaptor 50, except plunger 68 has been omitted. In this arrangement, advancement of a carrier 460 along a ramp 456 in direction A includes manually pushing a push surface 424A of head 424 via application of an appropriate force on head 424. For example, a medical professional may push or depress push surface 424A so as to urge carrier 460, and sheath 402 coupled thereto, in the direction A. In order to withdraw carrier 460, the user may apply an oppositely directed force (e.g., a lifting or upward force) on a lift surface 424B, so as to move carrier 460, and sheath 402 coupled thereto, in a direction opposite that of direction A.

Figure 8:
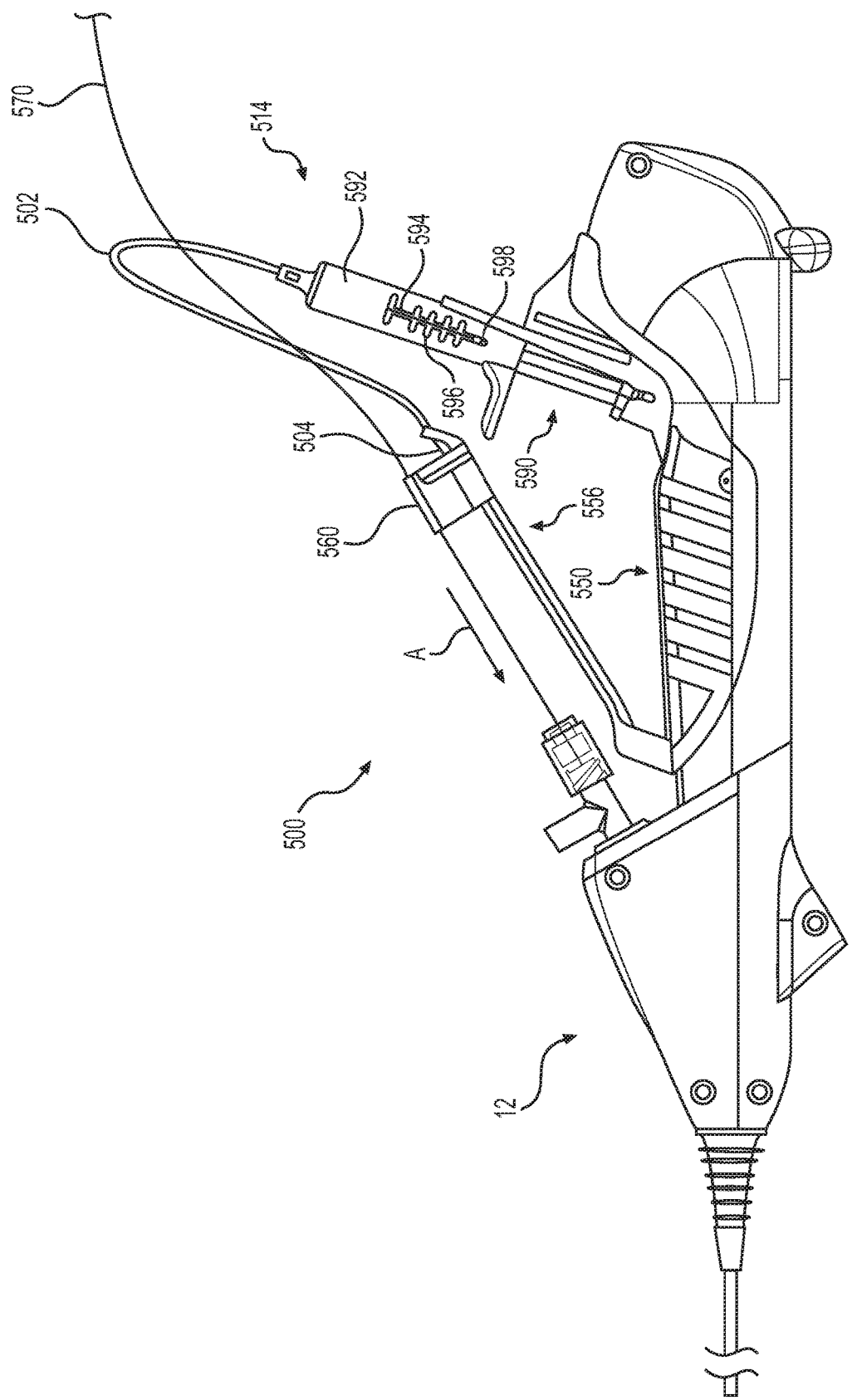
FIG. 8 illustrates an exemplary system according to another aspect of the present disclosure.

FIG. 8 illustrates a further an exemplary system 500 according to another aspect of the present disclosure. Similar to system 10, system 500 includes an adaptor 550 which is shown coupled to insertion device 12. Additionally, similar to adaptor 450, adaptor 550 omits a plunger. As shown in FIG. 8, adaptor 550 includes a handle of a medical device 514 including a plunger 590 and a slot body 592 moveable with respect thereto. Plunger 590 includes a protrusion or pin 598 located within a track 594 or one of the plurality of slots 596. Interaction between pin 598 and track 594 and/or slots 596 may guide movement of slot body 592 relative to plunger 590. Further, slot body 592 is coupled to a sheath 502 while an end of plunger 590 is coupled to a shaft 504. In use, depression of slot body 592 (coupled to sheath 502) relative to plunger 590 (coupled to shaft 504) results in retraction of sheath 502 relative to shaft 504, thereby increasing an exposed portion of cable shaft 504 extending distally of sheath 502. Increased extension of shaft 504 relative to sheath 502 permits movement of carrier 560 relative to ramp 556 in direction A. Additionally, as shown, carrier 560 is coupled to a laser fiber 570 in a manner similar to coupling of sheath 102 to carrier 60 of FIG. 1A. As such, advancement of carrier 560 in direction A results in likewise advancement of laser fiber 570 (or any other such device coupled to carrier 560) in direction A. In such an arrangement, the handle of medical device 514 may be used to advance and retract carrier 560. That is, the handle of medical device 514 may include an incremental slot in slot body 592 so as to aid advancement and retraction of laser fiber 570 incrementally.

Figure 9:
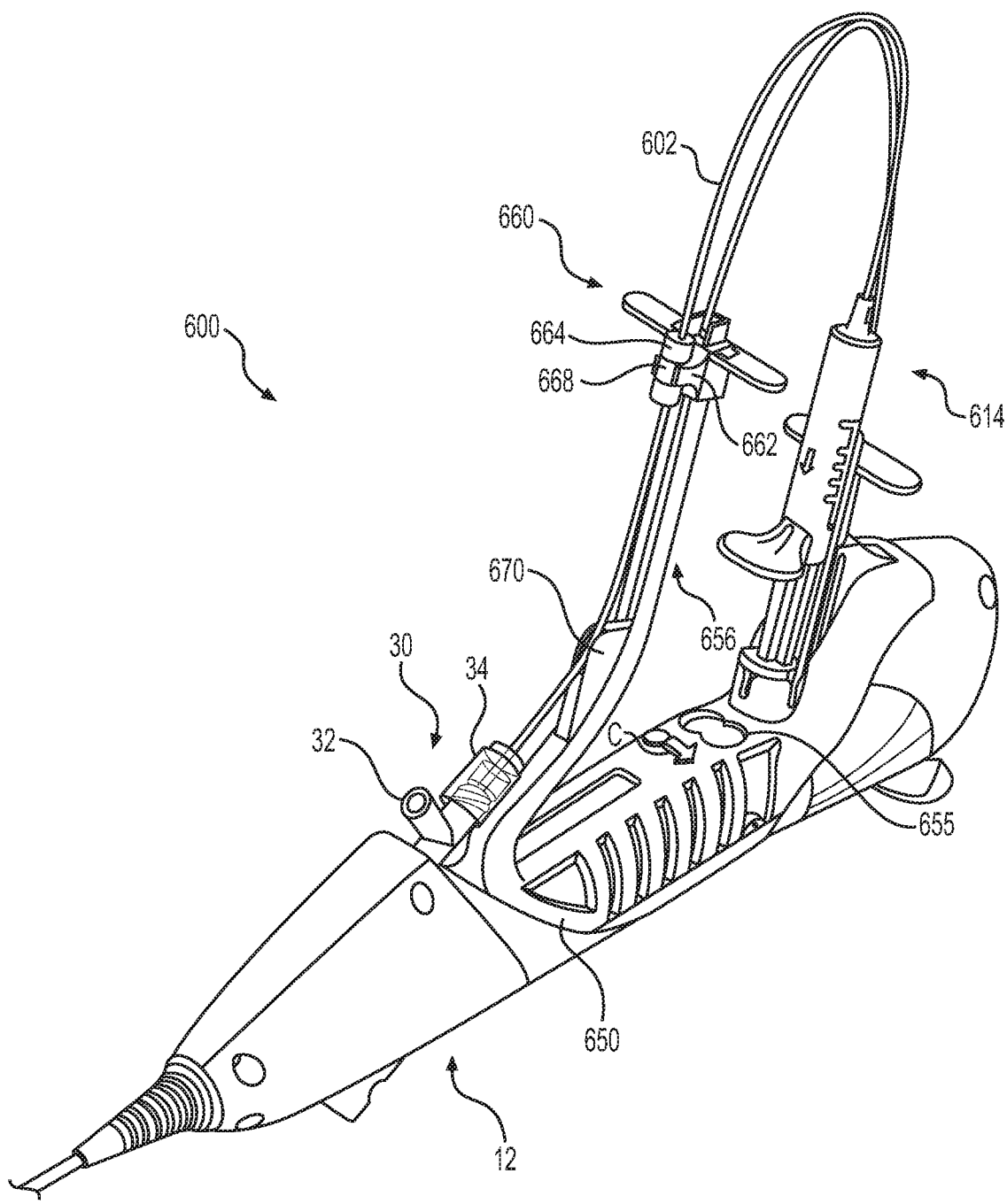
FIG. 9 illustrates an exemplary system according to a further aspect of the present disclosure.

In a further system 600, as shown in FIG. 9, a ramp 656 of an adaptor 650 extends generally parallel with a medical device 614. Such an arrangement may facilitate an increasingly ergonomic grip on adaptor 650, and/or insertion device 12 to which adaptor 650 is coupled. Additionally, such an arrangement may enable quicker manual actuation of a carrier 660 (e.g., similar to the manual actuation of carrier 60 or carrier 460, described above) of adaptor 650. While a generally parallel arrangement is illustrated, in other aspects, the alignment of ramp 656 may be adjusted to accommodate various medical professional's preferences and/or hand size. However, as opposed to the arrangements shown in FIGS. 1A, 1B, 2, ramp 656 does not extend at an angle generally parallel with an angle of second branch 34, and sheath 602 of medical device 614 must be bent prior to entering second branch 34. Accordingly, adaptor 650 may further include a support guide 670. As shown, support guide 670 may be an angular support member configured so as to redirect an angle of sheath 602 prior to entrance into second branch 34. That is, support guide 670 may be curved to adjust the angle of sheath 602. While support guide 670 is shown as having an open (e.g., u-shaped or c-shaped) channel within which sheath 602 may be received, the disclosure is not so limited. Rather, support guide 670 may include a closed channel (e.g., a fully enclosed lumen) through which sheath 602 may be passed prior to entrance into second branch 34. In either such arrangement, support guide 670 may facilitate accurate insertion of sheath 602 through port coupling 30.

Additionally, rather than channel 130 lined with silicone or other such material 132 (as described above in connection with FIG. 4), carrier 660 includes a mount 662 defining a recess within which a dumbbell coupler 664 of sheath 602 may be removably received. That is, coupler 664 may be fixed (e.g., glued) at a desired location along a length of sheath 602. As shown, coupler 664 may include a narrowed or recessed portion 668 which may be received within mount 662 of carrier 660. Such a connection may provide a friction or snap-fit coupling of sheath 602 with carrier 660. In such a manner, sheath 660 may be readily coupled and uncoupled from carrier 660.

In further aspects, any of the sheaths 102, 202, 402, 502, and 602 may be replaced with a stiffening sheath and/or a plurality of co-axial sheaths so as to impart increased stiffness, thereby enhancing accurate advancing and retracting of such a sheath via at least one of carriers 60, 260, 360, 460, 560, or 660. Additionally, any of the shafts and/or cables described herein may be comprised of any appropriate material such as, e.g., Nitinol. Moreover, all of the arrangements described herein enable a single operator and/or a single hand of a single operator to manipulate both an insertion device 12, as well as a medical device such as any of medical devices 14, 214, 414, 514, or 614. Additionally, any of adaptors 50, 250, 450, and 650 may be operated while uncoupled from an insertion device. As such, if the medical professional so desires, operation of adaptors 50, 250, 450, and/or 650 may be done via the medical professional's secondary hand or via an assisting medical professional.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

I claim:

1. An adaptor, comprising:
a shell;
a first plunger positioned at a first end of the shell and moveable between an undepressed state and a depressed state;
a ramp extending from a second end of the shell; and
a carrier coupled to the ramp;
wherein, in the undepressed state, the carrier is located at a first position along the ramp, and wherein, in the depressed state, the carrier is located at a second position along the ramp, wherein the second position is closer to the second end of the shell than the first position,
wherein the adaptor is configured to protrude from a handle of an imaging device and the shell is configured to be mounted onto the handle of the imaging device.

2. The adaptor of claim 1, further including a cable coupled to the carrier and a sleeve coupled to the ramp.

3. The adaptor of claim 2, wherein in the depressed state, more of the cable extends exterior of the sleeve than in the undepressed state.

4. The adaptor of claim 1, wherein the first plunger is snap-fit or friction fit within a channel of the adaptor.

5. The adaptor of claim 1, wherein the ramp includes at least one rail received within a channel of the carrier.

6. The adaptor of claim 1, wherein the ramp includes a curved support guide.

7. The adaptor of claim 1, wherein the adaptor further includes a medical device handle coupled thereto.

8. The adaptor of claim 7, wherein the medical device handle includes a sheath moveable with respect to a shaft between a collapsed configuration and an expanded configuration.

9. The adaptor of claim 8, wherein the sheath of the medical device handle is removably coupled to the carrier.

10. The adaptor of claim 7, wherein the medical device includes a second plunger that is stationary relative to the shell and the ramp and a body movable with respect to the stationary second plunger.

11. An adaptor, comprising:
a shell extending between a first end and a second end;
a plunger positioned at the first end of the shell moveably received within a channel of the shell, and moveable between an undepressed state and a depressed state;
a ramp extending from the second end of the shell, the ramp including a free end uncoupled to a remainder to the shell;
a carrier movably coupled to the ramp;
a sleeve having a sleeve length extending from a first end of the sleeve coupled to the free end via a slot of the carrier to an opposite end of the sleeve coupled to the plunger via a slit; and
a cable extending from an end of the channel, through the plunger, and coupled to the carrier, wherein the cable is movably received within the sleeve,
wherein, in the undepressed state, the carrier is located at a first position along the ramp, and wherein, in the depressed state, the carrier is located at a second position along the ramp, wherein the second position is closer to the second end of the shell than the first position, and wherein the adaptor is configured to be directly coupled to a handle of an imaging device and the shell is configured to be mounted onto the handle of the imaging device.

12. The adaptor of claim 11, wherein the plunger is moveable relative to the cable.

13. The adaptor of claim 11, wherein the ramp includes a curved support guide.

14. The adaptor of claim 11, wherein the plunger is snap-fit or friction-fit within the channel.

* * * * *